United States Patent [19]
Poussin

[11] Patent Number: 5,202,097
[45] Date of Patent: Apr. 13, 1993

[54] REACTOR WITH A LOWER WALL AND/OR AN UPPER WALL HAVING A LAYER OF A FLEXIBLE REFRACTORY MATERIAL

[75] Inventor: Bernard Poussin, Carrieres Sur Seine, France

[73] Assignee: Institut Francais du Petrole, France

[21] Appl. No.: 715,191

[22] Filed: Jun. 14, 1991

[30] Foreign Application Priority Data

Jun. 15, 1990 [FR] France ............................ 90 07614
Jun. 15, 1990 [FR] France ............................ 90 07615
May 16, 1991 [FR] France ............................ 91 05997

[51] Int. Cl.$^5$ ............................ B01J 35/02; B01J 8/02
[52] U.S. Cl. .................................. 422/218; 422/179; 422/181; 422/221; 422/239
[58] Field of Search ............ 422/217, 218, 221, 239, 422/240, 241, 310, 311, 148, 177, 179, 211, 181

[56] References Cited

U.S. PATENT DOCUMENTS

| | | | |
|---|---|---|---|
| 2,961,304 | 11/1960 | Collins | 422/217 |
| 3,167,399 | 1/1965 | Hansen, Jr. | 422/218 |
| 3,249,405 | 5/1966 | Waddill | 422/217 |
| 3,865,555 | 2/1975 | Elebracht et al. | 422/311 |
| 4,199,545 | 4/1980 | Matovich | 422/240 |
| 4,208,373 | 6/1980 | Matovich | 422/241 |
| 4,244,922 | 1/1981 | Burke et al. | 422/221 |
| 4,374,095 | 2/1983 | Legg et al. | 422/218 |
| 4,876,072 | 10/1989 | Checki | 422/221 |
| 4,929,429 | 5/1990 | Merry | 422/221 |
| 5,063,028 | 11/1991 | Humble et al. | 422/241 |

Primary Examiner—Michael G. Wityshyn
Assistant Examiner—William H. Beisner
Attorney, Agent, or Firm—Millen, White, Zelano & Branigan

[57] ABSTRACT

The invention relates to a reactor for carrying out gas phase chemical reactions and having at least one compartment (8) incorporating a catalytic lining (31) in which radially circulates at least one gas. As the upper wall (32), it has at least one layer (19) of at least one flexible material such as a tight, inert, refractory material fabric. This fabric optionally cooperates with a first layer of balls (12) resting on the fabric. It is placed on the biller (31) in such a way that it completely covers the latter. The reactor is used in the reforming of fuels.

23 Claims, 2 Drawing Sheets

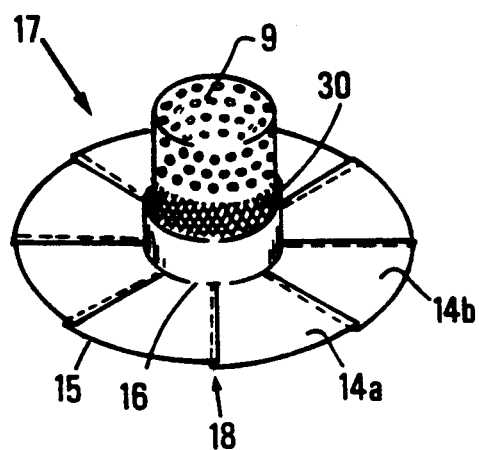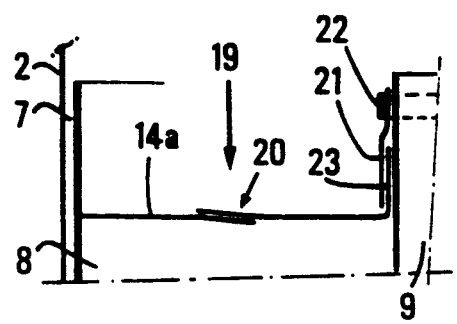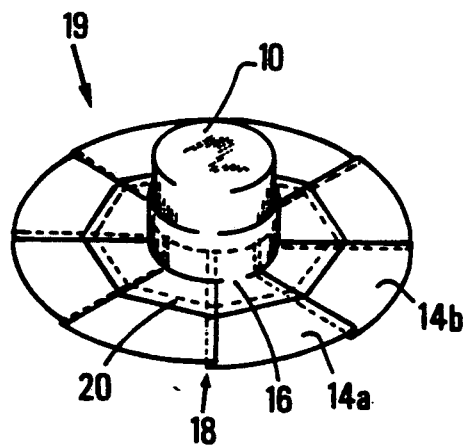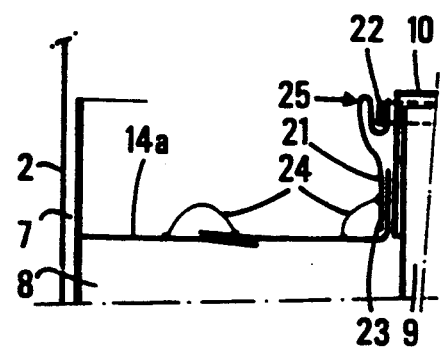

REACTOR WITH A LOWER WALL AND/OR AN UPPER WALL HAVING A LAYER OF A FLEXIBLE REFRACTORY MATERIAL

SUMMARY OF THE INVENTION

The present invention relates to a reactor for carrying out gas phase chemical reactions at a given temperature and pressure and to the use thereof. It also relates to a reactor for filtering particles in a liquid phase. This reactor operating in the gas phase can be used for the reforming of petroleum fractions, for the aromatization of petroleum fractions and for the synthesis of methanol.

The invention more particularly relates to vertically axed reactors having at least one compartment filled with a bed of particles traversed by a single-phase fluid, which is preferably gaseous and able to operate at a pressure of, e.g., 1 to 200 bar.

The prior art is illustrated by the patent U.S. Pat. No. 2,961,304 wherein the pressure drop is diminished by filtration of the gaseous or liquid feed which is introduced at the bottom of the reactor. This pressure drop is also diminished by avoiding fluidization of the particles with an anti-fluidizing zone consisting of a layer of packed inert particulate solids atop a layer of knitted wire mesh bearing upon the top surface of the bed of contacting particles. Therefore, the anti-fluidizing zone is not tight and not supple.

It is known from the prior art to use a radial reactor having a cylindrical shape, where the fluid is introduced by a ring close to the collar or sleeve in the shape of an annular, catalyst-based particulate lining. This fluid passes radially through the catalytic bed and the effluent is collected in a perforated central stack, where it is then discharged.

The head or top of the particle compartment is generally constituted by a cap or cover covering the stack, which is introduced into the catalyst bed and an assembly incorporating a cover and a skirt constituted by dismantlable, bolted sectors, which enter the catalyst bed surmounted by a layer of inert balls having an appropriate grain size. This skirt enters the bed over a length of approximately 0.5 times the thickness thereof, said penetration representing the minimum which must remain after the assumed recompressing of the catalyst bed after bringing the apparatus to the appropriate temperature and pressure, in order to make the gas flow traverse the bed thickness at least once.

This design leads to assembly and installation constraints. It is difficult to adjust the various elements and it is necessary to cut or lengthen the skirt as a function of the catalyst quantity to be charged, its intrinsic density and its filling density, while considering the problems linked with the weakening of the bolt system after use.

Moreover, in the head or top of the bed, the catalyst quantity trapped inside and outside the skirt has little or no action, so that a generally costly catalyst volume, which can represent 8 to 15% of the total volume of the catalyst, is not used, which is prejudicial to the economics of the process performed.

The situation is the same at the bottom of the bed. The safety height for the collecting means on the base of the stack, corresponding to the bed height traversed by the gaseous effluent, so that it passes through the bed thickness at least once, creates a dead zone which is prejudicial to the economics of the process.

A first object of the invention is to avoid these dead zones at the top of the bed in the particulate compartment. Another object is to avoid dead zones at the bottom of the bed, said two objects making it possible to achieve the maximum filling capacity of the compartment and an optimization of its use.

Another object of the invention is to have a filling flexibility for the compartment, which is a function of the desired demand and with a minimum of constraints and therefore increased speed.

Another object of the invention is to be able to adapt the covering of the bed to the lining volume during the operation of the reactor as regards temperature and pressure and in general terms, no matter what the gas or liquid charge type, to follow the compression of the bed by a new flexible covering adapting to the bed shape in accordance with an overall radial plane.

Another object of the invention is to avoid the presence of balls or particles resting on the catalyst bed and to separate the balls and the catalyst during discharging.

Therefore the invention proposes a new compartment covering having a filler, which in particular avoids the passage of the gas along an overall axial path and aids the passage through the filler thickness in a substantially radial manner.

More specifically, the invention relates to a reactor for performing gas phase chemical reactions at a given temperature, or for filtering at least one fluid containing solid particles, which has at least one compartment (8) with at least one filler (31) of particles, in which radially or transversely circulates at least one gas or liquid. The compartment also has an upper wall (32), which is, at least one layer of at least one appropriately shaped flexible, refractory material (19), which is substantially inert and substantially impermeable or having a texture and a porosity such that the layer creates a pressure drop greater than that produced by the particle lining, said material layer bearing on the particle filler (31) in such a way that it substantially completely covers the filler.

The term flexible material is understood to mean a fabric or a felt-type material, or superimposed fabric and felt-type material. The term appropriately shaped material is understood to mean a flexible material substantially adopting the geometry of the compartment cross-section, which can be square or rectangular and is advantageously annular.

By avoiding the presence of particulate material or balls, the available volume for the catalyst is maximized.

Advantageously, the flexible material layer can cooperate with a first substantially inert layer of balls (1, 12, 13) or a particulate material having an appropriate grain size and weight and which rests on the said material layer (19).

According to a first embodiment, said material can be constituted by a single piece or a plurality of sewn pieces arranged in such a way that they constitute a single substantially tight piece.

The reactor generally comprises at least one catalyst compartment, which can be parallelepipedic with a substantially rectangular or square cross-section. It can be substantially cylindrical with a substantially annular cross-section with a gas or liquid distribution envelope all around the cylindrical compartment and a substantially cylindrical central stack having effluent collecting means. The surface of the material layer is generally at least equal to the surface of the compartment in accordance with a radial or transverse plane occupied by the filler traversed by the gas or liquid. The stack can be covered by a metal cap or a cap made from the substantially tight, flexible refractory material, the layer of material constituting the top or roof of the compartment and the cap being made in one piece or a plurality of pieces, which are cut and adequately sewn in such a way as to be tight.

For ease of understanding, consideration will be given to the case where the filler is a catalyst traversed by a gas or a mixture of gases.

According to another embodiment, the reactor compartment can also have a lower wall (33) or floor with at least one layer (17) of said appropriately shaped flexible material, which optionally cooperates with a second substantially inert layer of balls (11, 12, 13) or a particulate material with an appropriate grain size and which rests on said second inert layer, so as to ensure a substantially total covering of the second layer.

According to a second embodiment, the reactor has as the upper wall at least one layer with a plurality of strips or pieces of refractory material fabric, which is substantially inert and substantially impermeable and which has a texture and porosity such that said strips create a pressure drop higher than that produced by the particulate filler, said strips optionally cooperating with a first inert layer of balls or a particulate material of appropriate grain size and weight and which rests on the said strips, being located on the filler in such a way that said strips ensure a substantially total coverage of said filler and they are at least partly superimposed so as to slide on one another in at least one direction. The term strips of material is understood to mean a section which can have both a substantially rectangular or square shape, or a shape corresponding to an annular sector.

Advantageously, the said strips cooperate with the first layer of balls or material with a better axial sealing and with a greater safety of use, the weight of the particles being added to that of the flexible material and to the pressure exerted by the charge on entering the reactor.

According to another embodiment, the reactor compartment can also have a lower wall or floor constituted by at least one layer having a plurality of strips of said material, said strips optionally cooperating with a second inert layer of balls or a particulate material of an appropriate grain size resting on said second inert layer in an arrangement such that the said strips ensure a substantially total coverage of the second layer and such that they can freely slide on one another in at least one direction.

In the absence of balls or particulate material, the flexible layer can rest on the reactor bottom, which can either be one or more metal plates, or a covering of the bottom by cement up to a substantially horizontal level.

According to a feature of the invention, the flexible material strips can define the superimposing zones, which have a width at least equal to the extent of the deformation which can be imposed by the lining. The partial covering of the underlying strips aids the free sliding of the strips and production of an adequate seal.

According to another feature of the reactor, a portion of a strip or a part of the said material can rest on a portion of a contiguous strip, so that a single layer forms the covering of the catalyst bed.

According to another feature, when the two layers of strips of the said material are superimposed, a strip of the upper layer can rest on a portion of the width of two contiguous strips of the lower layer and the said two strips may or may not be joined.

According to another feature, when the two strips of said material are superimposed, a portion of a strip and a portion of another contiguous strip of the upper layer can at least partly cover a strip of a lower layer.

In order to achieve the best results, it is advantageous to satisfy at least one of the following conditions:

a) the width of the covering zone of the strips is a function of the height H of the catalyst bed and which is normally between 0.001 and 0.2 H and is preferably between 0.01 and 0.1 H;

b) it can also be a function of one or other dimension of a strip, e.g. the covering zone can represent 0.05 to 0.5 times the length or width of a strip as a function of whether covering takes place in a respectively radial or circular direction and is preferably 0.1 to 0.2 times; and c) the covering surface can e.g. be between 0.05 and 1.5 times the surface of the bed and is advantageously between 0.1 and 0.5 times the bed surface.

The thus obtained axial sealing due to the pressure of the gases on entering and the weight of the particulate material on the covering of the bed and the absence of dead zones in the said bed make it possible to improve the efficiency of the zones traversed by a better use of the lining and in the present case the catalyst. Moreover, the apparatus construction is easy in that this light-weight equipment requires no special tools and requires only a short installation time. Thus, there is generally no need for an adjustment or recutting of the covering to be provided as a function of the definitive height of the catalyst, which is a function of the quantity desired by the client, the density of the catalyst and the density of the charge (dense charge or sleeve charge).

The proposed construction having a top or roof and optionally a catalytic compartment floor constituted by flexible material cooperating with the layers of balls is particularly suitable for small reactors, e.g., cylindrical reactors having a central stack and with a diameter of, e.g., 1400 mm, as well as for large reactors.

These advantageous variants with respect to the covering and floor of the annular compartment ensure the maintenance of the necessary seal in the upper part of the reactor during catalyst compression and prevent any catalyst from intruding into the lower part during charging.

According to another feature of the invention the flexible material layer can be constituted by at least one fabric or at least two fabrics of the same or different types and which are preferably assembled by stitching or sewing.

According to another feature of the invention said layer can be constituted by at least one felt-type material or at least two felt-type materials of the same or different types, preferably assembled by stitching or sewing. This material can be compressed to a variable extent so as to achieve a thickness, e.g., between 0.5 and 0.50 mm and an apparent density of, e.g., 0.05 to 0.25.

According to another feature of the invention said layer can be constituted by at least one fabric and at least one felt-type material, the fabric and the felt-type material advantageously being assembled by sewing.

Excellent results are obtained when the said layer comprises a sandwich structure, i.e., at least one felt-type material placed between at least two fabrics, advantageously assembled by sewing.

For example, if T is the fabric and F is the felt, it is possible to have a stack such that T, F, T or TFFT, or TFTFT or TTFTT or TT, FF, TT.

Fabric is understood to mean a material obtained by the assembly of intertwined threads of the same or a different nature. A felt-type material is one obtained by the intimate aggregation of flocks and/or filaments of the same or a different nature.

When the covering of the compartment is constituted by superimposed strips, the size thereof once the said strips are in place can exceed the thickness of the filler which the charge has to traverse. In this case, the end of each strip or annular sector, e.g. on the stack side, can be covered by a ring of said flexible, refractory material, whereof the upper part can be fixed to the stack by any appropriate means and with a lower portion placed above the said end in such a way that the ends of the strips or annular sectors slide beneath the ring. According to another variant, the end of each strip on the stack side can cover the lower portion of said ring, so that there is a possibility of said end sliding on the said ring.

The fabric used according to the invention is constituted by generally made from a ceramic material and having a good tensile strength even at high temperature, e.g. 15,000 to 28,000 kg/cm$^2$ between 370° and 540° C. They generally have a porosity between 2 and 8% and advantageously between 3 and 5%. They are flexible and resistant to deformations. They are able to withstand temperatures higher than 1200° C. They can be combined with other oxides of metals (alkali metal, alkaline earth, iron, titanium, boron in exemplified manner) increasing their mechanical strength and/or their sealing. For example, use is made of the textile ZETEX ®, whose fiber composition is advantageously as follows:

| | |
|---|---|
| silicon oxide | 52 to 60% |
| calcium oxide | 16 to 25% |
| aluminium oxide | 10 to 13% |
| boron oxide | 8 to 13% |
| sodium oxide | 0 to 1% |
| magnesium oxide | 0 to 6% | and whose tensile strength is e.g. approximately 17,400 kg/cm$^2$ at 540° C.

According to another variant of the invention, the fabric can be made substantially tight by the deposition of e.g., an aluminium-Mylar layer. It is possible to use a knitted fabric based on stainless refractory steel wires, e.g., 304 L or 316 L manufactured by GANTOIS, Saint Die, France.

It is also possible to use the fabric KATISS constituted by a KERLANE 45 ceramic fiber layer, which is able to withstand a temperature of more than 1260° C. and which is reinforced on its two faces by a glass fabric E (sillicone) of porosity 2 to 5%. Generally the composition is as follows:

| | |
|---|---|
| Al$_2$O$_3$ | 47% |
| SiO$_2$ | 52% |
| Fe$_2$O$_3$ + TiO$_2$ | ≦0.20% |
| CaO + MgO | ≦0.15% |
| Na$_2$O + K$_2$O | ≦0.25% |

The composite fabric of CERAFIBER refractory fibers reinforced by Inconel filaments able to withstand temperatures up to 1260° C. in a normal oxidizing atmosphere can also be used and comprises:

| | |
|---|---|
| Al$_2$O$_3$ | 46.5% |
| SiO$_2$ | 53% |
| Fe$_2$O$_3$ | 0.1% |
| TiO$_2$ | 0.05% |
| MgO | 0.01% |
| CaO | 0.04% |
| Na$_2$ + K$_2$O | 0.2% |

Excellent results were obtained with HEXCEL GENIN 1003 fabrics and in particular with HEXCEL GENIN 1217 fabrics produced by HEXCEL GENIN, Decines-Charpieu, France, between which is sandwiched a KERLANE 45 ® felt-type material.

The composition of these fabrics and felt is given in the following table:

| | SiO$_2$ | Al$_2$O$_3$ | B$_2$O$_3$ | CaO | MgO | TiO$_2$ | Na$_2$O | C |
|---|---|---|---|---|---|---|---|---|
| Hexcel Genin 1003 | 83.98 | 0.66 | 0.20 | 0.42 | <0.05 | 0.35 | <0.05 | <0.2 |
| Hexcel Genin 1217 | 24.17 | 62.37 | 15.62 | <0.05 | <0.05 | <0.05 | <0.05 | <0.2 |
| KERLANE 45 ® | 52 | 47 | | <0.15 | <0.15 | <0.2 | <0.25 | |

As an example of a metallic felt, reference is e.g. made to the stainless steel BEKAERT 316 L felt.

The balls or particulate material placed in at least one layer on the fabric covering of the catalyst bed, or on which the fabric floor according to the invention rests are generally substantially inert. They can be constituted by a catalyst support. When one or more layers are used, the layer in contact with the flexible material according to the invention generally has a low grain size, e.g. 0.5 to 0.8 cm, whilst the grain size of the other layer, when there are two such layers, can e.g. be 2 to 3 cm. Balls made from alumina or a mixture of alumina and silica oxide may be used.

BRIEF DESCRIPTION OF THE DRAWINGS

The invention is described in greater detail hereinafter relative to non-limitative embodiments of the reactor and with reference to the attached drawings, wherein is shown:

FIGS. 8 and 9—The catalyst bed top and bottom with a plurality of superimposed strips of an appropriate fabric.

FIG. 10—A variant with sliding of the fabrics, maintaining sealing along the central stack.

FIG. 11—Example of superimposing fabric strips.

DETAILED DESCRIPTION OF THE DRAWINGS

Figure 1:
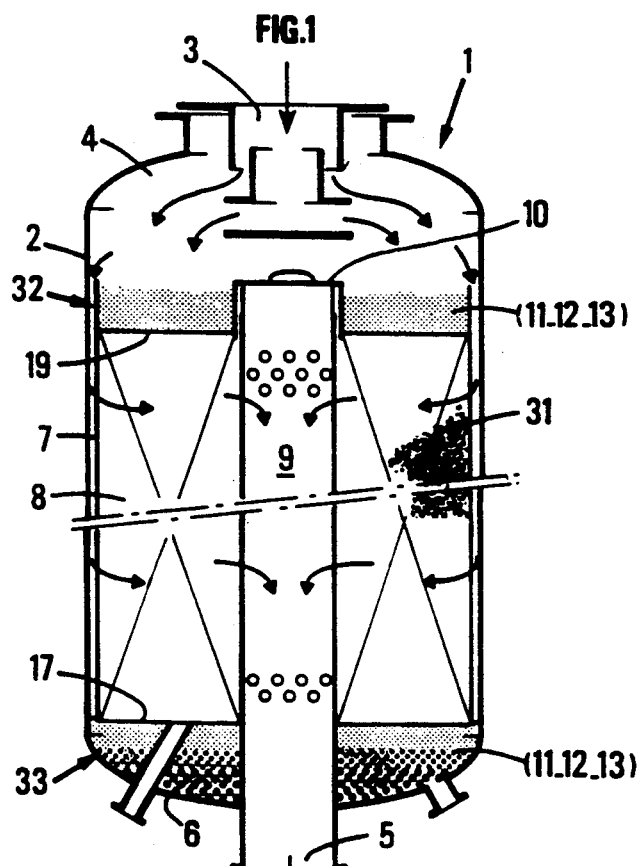
FIG. 1—A longitudinal section of a radial reactor.
Figure 2:
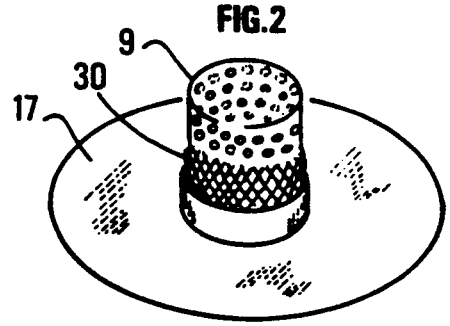
FIGS. 2 and 3—The top and bottom of the catalyst bed with respectively a fabric portion and a plurality of fabric portions assembled by sewing.
Figure 3:
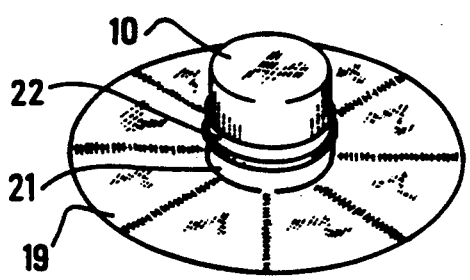

According to FIG. 1, a radial cylindrical reactor (1) able to operate under high temperature and pressure comprises a cylindrical metallic sleeve or collar (2) with an inlet (3) for the gaseous charge level with the upper end (4) and an effluent outlet (5) level with the lower end (6). All around the sleeve and wedged within the reactor is provided an annular ring (7) with openings, which serves to distribute the charge in a substantially radial manner in an annular catalytic compartment (8). The catalyst is constituted by a bed incorporating balls, pellets or more generally rodlets with a diameter of 1 to 2 mm and a length of 4 to 6 mm. After radially traversing the catalyst bed, the effluent is recovered by a cylindrical central stack (9), which is generally a perforated tube covered by a grid (30) (FIG. 2) and which is evacuated by the outlet (5). Above the stack, a metal cap (10) surrounding the upper part thereof, is immersed in the catalyst bed and seals the stack with respect to the charge.

The lower end (6) of the reactor (FIG. 2) is filled to a thickness of 50 cm of balls (11) made from alumina or alumina-silica oxide ceramics, e.g. with an approximate grain size of 1.9 cm and on which rests another thickness of 10 cm of balls (12) of substantially the same nature and with a grain size of approximately 0.63 cm and finally a third thickness of 5 cm of inert catalyst support (13). On said third thickness is placed a layer constituted by two fabric thicknesses (17) of Hexcel Genin 1217®, ceramic material fibers, sandwiching a thickness of a felt-type material (KERLANE 45®) assembled by sewing. For reasons of simplicity, the assembly will be referred to as fabric throughout the description. This substantially tight layer is constituted by a single substantially annular piece, which has been cut to the shape of the surface of the compartment. Preferably, this layer is cut to provide a surface larger than that which is necessary for covering the compartment, so that at least one end, preferably on the stack side, can be straightened or trued against the wall thereof. The catalyst rests on the fabric and its weight contributes to the axial sealing of the lower wall of the compartment.

The upper reactor end (4) has above the catalyst bed on which it bears, a layer of the material according to the invention (19), which is of the ceramic substance described hereinbefore. A first thickness of 10 cm of balls (11) or a particulate material having a grain size of e.g. 1.9 cm and a second thickness of 10 cm balls (12) in contact with the fabric layer and with a grain size of, e.g., 0.63 cm rest on the fabric. These two layers exert on the bed a uniformly distributed charge and with the fabric layer contribute to giving an axial sealing to the bed. The gaseous flow must pass round the covering as soon as it enters the reactor in order to laterally come into contact with the catalyst bed, said flow circulating radially or transversely from top to bottom towards the outlet.

The flexible layer is constituted by a plurality of pieces of the said material, each having an annular sector shape, which are placed end to end so as to be sewn together in known manner by a filament which cannot be destroyed by heat. The flexible layer of fabrics can be fixed by appropriate means, such as bolts, to a base produced in the lower part of the cap covering the stack. According to another fixing procedure, a ring (21) of said material according to the invention can be placed by means of a locking ring (22) against the cap (10) covering the stack and can be sewn to the different annular sectors in such a way that the ring and the fabric layer covering the catalyst bed form a single piece. The excess part of the fabric brought against the stack and represented by the ring (21) not having a locking ring (22) can be covered, in the manner shown in FIG. 4, by another fabric ring (21a), whose upper portion adheres to the stack (9) or to the cap (10) by means of another locking ring (22) where the remainder covers the corresponding end at the excess portion of the fabric. Thus, a deformation of the catalyst bed surface as a result of a possible compression of the catalyst can be compensated by the sliding of the fabric applied to the cap or the stack beneath the ring.

Figure 5:
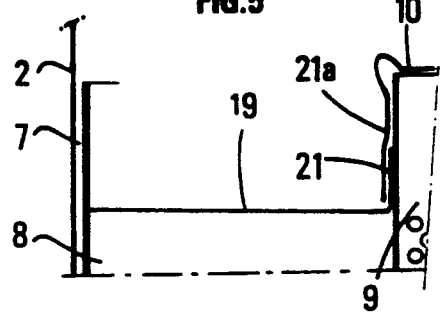

The fabric ring (21a), which is free from any movement, can also constitute the cylindrical portion of a refractory fabric cap (10) according to the invention and as is shown in FIG. 5, which covers the stack (9) and the fabric portion of the ring (21) slides beneath the cap ring (21a).

Figure 6:
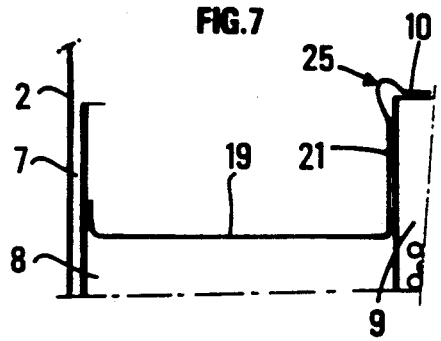

According to FIG. 6, the end of the fabric applied to the stack or cap corresponding to the excess portion compared with the surface of the catalyst bed is adjusted so as to have a length enabling it to form a safety margin (25) making it possible to remedy any catalyst compression or packing action.

Figure 7:
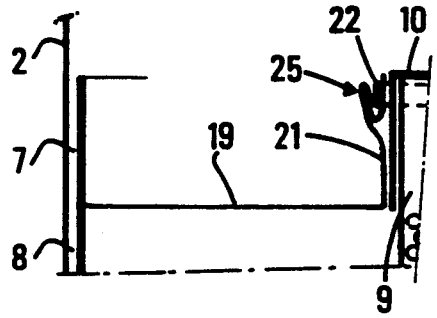

Finally, according to FIG. 7, the catalyst bed covering (19), the ring (21) and the cap (10) with its safety margin can form an assembly of a single fabric piece appropriately arranged and made tight by known seams. This technical solution is advantageous, because said assembly can be very easily installed and removed from the reactor.

Figure 4:
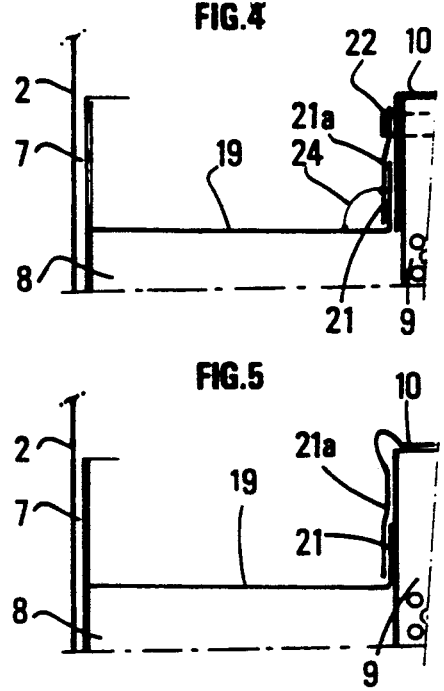
FIGS. 4, 5 6 and 7—Variants where sealing is maintained along the stack or along the cap covering the stack of the annular reactor.

According to a special embodiment, the fabric layer and the ring (21a) can be connected by a filament (24), which cannot be destroyed by heat, so as to be easily refitted with the stack or its cap (FIG. 4).

The case where the excess portion of the fabric layer has been applied to the stack or cap is illustrated. It is obvious that an excess portion of the strip can optionally be applied to the outer charge distribution ring, so as to fulfil a safety function and as is illustrated in FIG. 7.

According to the second embodiment, the references of FIGS. 1 to 7 are used for FIGS. 8 to 11 for indicating the same means.

Placed on the third layer of balls constituted by the inert catalyst support having the lower end (6, FIG. 1) of the reactor are placed strips of the material according to the invention forming a flexible layer (17), which are in the form of annular sectors (14a, 14b), whose end (15), on the charge distribution ring side, is substantially in contact with the said ring (7) and whose end (16), on the stack side, is straightened towards the top of the reactor and applied over a height of approximately 8 cm to the stack (9).

The different annular sections (14a and 14b) are superimposed over part of their width in such a way that they form the layer (17) with superimposed zones (18) in accordance with a circle, whereof the covering width is at least equal to the extent of the deformation which can be imposed, so that axial sealing is ensured. The catalyst rests on said fabric layer (17) and its weight contributes to the axial sealing of the lower wall of the compartment.

The upper end (4) of the reactor has, above the catalyst bed on which it bears, a layer (19) of the flexible assembly of fabrics and felt in sandwich form described hereinbefore and on which rests the layers of balls and which, together with the flexible layer strips, ensure an axial sealing of the bed.

The upper wall of the compartment (FIG. 9) or the top of the bed (32) consequently comprises a layer (19) constituted by a plurality of strips (14a) of the flexible material, which has an overall annular shape in order to adapt to the surface of the compartment which they cover. These different strip sections (14a, 14b) are arranged so as to define superimposing zones (18), whose covering width is at least equal to the extent of the deformation which can be imposed by the filter during the reaction or as a result of an untimely manipulation.

The superimposing of the strips can also be radial and the covering zone (20) can have a width at least equal to the deformation which can be imposed by the filler. It follows that the total surface of the plurality of strips arranged in this way e.g. exceeds by approximately 50% the annular surface of the catalyst compartment.

The strips on the stack side can be fixed by adequate means, such as bolts, to a base formed in the lower part of the cap covering the stack.

In FIG. 10, the length of the strips constituting the covering in the radial direction of the compartment can exceed the thickness of the catalyst bed, e.g., by 40 to 50 cm. For example, the end at the stack side corresponding to the excess portion (23) is straightened towards the top of the reactor and is engaged against the stack (9). It is covered by a ring (21) made from the material according to the invention, whose lower portion covers the raised excess portion in such a way that the latter slides beneath the ring as a function of the catalyst compression. This ring can adhere to the central stack (9) by its upper portion, which can be fixed by a locking ring (22) or by a ceramic fiber cord. A metal cap (FIGS. 6 and 10) can cover the upper portion of the stack. It generally adopts the substantially cylindrical shape of the stack and is substantially tight with respect to the gas and the effulent. Under these condition, it has the advantage of a very limited height. This tight cap can also be constituted by the flexible ceramic material according to the invention.

According to another embodiment, similar to that of FIG. 5, the excess portion (23) of the strips is applied to the stack (9) and covered by the cylindrical portion or ring of a substantially tight ceramic material cap (10) covering the stack. This cap has at least one bead, so that it can be elongated, as in the case of FIG. 6.

According to a variant illustrated by FIG. 11, the length of the strips in the radial direction of the compartment can exceed the thickness of the catalyst bed, e.g., by 20 to 30 cm. The stack side end can then be straightened or trued towards the top of the reactor and engaged against the stack cap. A substantially rectangular strip of the same material is applied to the straightened portion (23) of the strip, thus forming the ring (21). Its upper portion adhering to the cap by a locking ring or by a non-destructible, ceramic material cord or string ensures that the strip constituting the roof of the compartment can slide along the cap in accordance with the catalyst compression.

According to a variant of the apparatus illustrated by FIGS. 8, 9 and 10, a portion of the strip can rest on a portion of a contiguous strip in such a way that the covering of the compartment is ensured by a layer of fabric strips able to slide on one another in a circular direction (FIG. 8) and/or a radial direction (FIGS. 9 and 10).

According to a variant of the apparatus, two fabric strip layers can be superimposed. An upper layer strip rests on a portion of the width of two contiguous strips of the lower layer and said two strips may or may not be joined. The covering plane obtained according to these two variants can be horizontal or inclined towards the envelope or stack.

Strips on the envelope side can be cut so as to adopt the shape of the distribution means. It is therefore possible to add elements which adopt the shape of the said means and which are superimposed on the fabric strips.

In general terms, the putting into place of the top or bottom of the compartment can be carried out in the manner indicated hereinbefore and a radial and optionally circular stitching of the fabric elements in superimposed form is carried out by the generally autodestructible thread during said putting into place. The stitching threads connecting the various strips would lose all resistance and strength following the catalyst bed temperature rise, so that the fabric strips slide on one another to give the necessary flexibility to the thus formed assembly. According to an embodiment illustrated in FIG. 11, the different strips or constituent elements of the covering of the bed or the bottom of the bed can be joined together by a non-destructible connecting thread (24), which generally has a length at least equal to the dimension of the superimposed zones, which facilitates their recovery during reactor discharging. These different strips can also be connected by any appropriate means to the stack cap. Thus, when the latter is fitted again, it can move the bed covering.

According to another embodiment, the strip portion (23) applied to the stack or stack cap can have a safety margin (25) ensuring a greater freedom of movement. This margin (25) can also be located on the ring (21) covering the excess portion of the strips trued against the stack or cap (FIG. 11), as a function of the chosen embodiment.

FIG. 1 shows balls or particles (11, 12) resting on the flexible layer (19) in the form of the upper wall (32), but it would also be possible to show the latter without balls or particles. In the same way, the lower wall (33) could be shown without the various layers of balls (11, 12, 13), the flexible material layer resting directly on the cement filling the bottom of the reactor up to a substantially horizontal level.

I claim:
1. An apparatus for carrying out gas phase chemical reactions at a given temperature comprising:
 a reactor vessel;
 a first sleeve positioned in said vessel so as to define an annular fluid distribution envelope between said first sleeve and an interior of said vessel;
 a second sleeve positioned in said vessel so as to define an annular space between said first sleeve and said second sleeve, said first sleeve and said second sleeve being permeable to a reaction fluid;
 upper and lower walls sealing said annular space so as to define an annular compartment, said annular compartment being filled with reaction catalyst particles;
 a feed inlet in flow communication with said distribution envelope such that introduced reaction fluid radially or transversely circulates through said compartment; and said upper wall comprising at least one layer of at least one flexible refractory material which is inert to the chemical reaction and impermeable to the reaction fluid and which has a texture and porosity such that the presence of the layer produces a pressure drop higher than that produced by the compartment of catalyst particles.

2. An apparatus according to claim 1, further including a first layer of inert particulate material positioned on said layer of flexible material.

3. An apparatus according to claim 1, wherein said lower wall comprises at least one layer of said flexible material and further includes a second layer of inert particulate material positioned between said lower wall material and said vessel.

4. An apparatus according to claim 1, wherein said layer is defined by a single piece of said flexible material or a plurality of pieces of said flexible material sewn together so as to form a single piece.

5. An apparatus according to claim 1, wherein said layer is defined by a plurality of separate sections of said material which are at least partly superimposed on one another so as to slide with respect to one another while maintaining the pressure drop of the layer.

6. An apparatus according to claim 5, wherein the said sections are superimposed with a width sufficient to maintain the pressure drop of the layer to the extent of deformation which can be imposed by the catalyst particles.

7. An apparatus according to claim 5, wherein said width is between 0.001 and 0.20 times the height of the catalyst particles.

8. An apparatus according to claim 5, wherein said width is between 0.05 and 0.5 times the length of the section in the direction of the desired sliding.

9. An apparatus according to claim 5, wherein an upper layer and a lower layer are defined by said sections, said sections being superimposed such that a section of the upper layer is positioned on a portion of the width of two contiguous sections of the lower layer.

10. An apparatus according to claim 5, wherein an upper layer and a lower layer are defined by said sections, said sections being superimposed such that a portion of a section and a portion of another contiguous section of the upper layer at least partly cover a section of the lower layer.

11. An apparatus according to claim 5, wherein said second sleeve defines a substantially cylindrical central stack having effluent collecting means, and wherein the size of the sections in accordance with the radius of the annular section is greater than the thickness of catalyst particles filling the section, the end of each section on the stack side being covered by a refractory fabric ring, the lower portion of which covers the end of each section, so that said end slides beneath the ring, or the end of each section on the stack side covers the ring such that said end slides on the ring.

12. An apparatus according to claim 11, wherein the ring has an upper portion adhering to the central stack.

13. An apparatus according to claim 11, wherein the stack is covered by a metal cap or by a cap made of the flexible refractory material.

14. An apparatus according to claim 11, wherein the stack is covered by a cap made of the flexible refractory material and the cap defines the ring.

15. An apparatus according to claim 11, wherein the end of each section is fixed to the stack or to a cap covering the stack.

16. An apparatus according to claim 11, wherein the ends of the sections are arranged by means of seams so as to define a cap covering the stack.

17. An apparatus according to claim 11, wherein the ends of the sections have a length such that they define a safety margin.

18. An apparatus according to claim 1, wherein the compartment has a substantially rectangular or square cross-section.

19. An apparatus according to claim 1, wherein said flexible material layer comprises at least one fabric.

20. An apparatus according to claim 19, wherein the fabric comprises ceramic material fibers.

21. An apparatus according to claim 19, wherein the fabric includes a layer of alumina positioned thereon.

22. An apparatus according to claim 1, wherein said flexible material layer comprises at least one felt-type material.

23. An apparatus according to claim 1, wherein said flexible material layer comprises at least one felt-type material arranged between at least two fabrics assembled by sewing.

* * * * *